(12) United States Patent
Pinyayev et al.

(10) Patent No.: US 9,956,586 B2
(45) Date of Patent: May 1, 2018

(54) METHOD FOR PRODUCING COMPOSITE STRUCTURES WITH A PLURALITY OF ABSORBENT FOAM PARTICULATES

(71) Applicant: The Procter & Gamble Company, Cincinnati, OH (US)

(72) Inventors: Aleksey Mikhailovich Pinyayev, Cincinnati, OH (US); Steven Ray Merrigan, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 146 days.

(21) Appl. No.: 14/937,362

(22) Filed: Nov. 10, 2015

(65) Prior Publication Data
US 2016/0136683 A1    May 19, 2016

(30) Foreign Application Priority Data
Nov. 14, 2014  (EP) .................................... 14193284

(51) Int. Cl.
*B05D 3/00*    (2006.01)
*A61F 13/532*    (2006.01)
(Continued)

(52) U.S. Cl.
CPC ........ *B05D 3/007* (2013.01); *A61F 13/15658* (2013.01); *A61F 13/535* (2013.01);
(Continued)

(58) Field of Classification Search
CPC ............ A61F 13/5323; A61F 13/53436; A61F 13/535; A61F 13/15658; B05D 3/007; B32B 2555/00; B32B 7/12; B32B 37/12; B32B 2307/726; B32B 27/12; B32B 27/32; B32B 29/005; B32B 29/007; B32B 29/02; B32B 2255/02; B32B 2262/02; B32B 2262/0253; B32B 2262/0276; B32B 2262/06; B32B 2262/062;
(Continued)

(56) References Cited

U.S. PATENT DOCUMENTS 4,338,366 A    7/1982 Evans et al.
4,892,535 A  *  1/1990 Bjornberg ......... A61F 13/15642
                                                604/366
(Continued)

OTHER PUBLICATIONS

PCT International Search Report, dated Jan. 20, 2016, 14 pages.

*Primary Examiner* — Vishal I Patel
(74) *Attorney, Agent, or Firm* — Andres E. Velarde

(57) ABSTRACT

Methods for producing composite structures with a plurality of absorbent foam particulates between substrates, wherein the method includes providing a carrier substrate. The carrier substrate may comprise a pre-determined pattern. The pre-determined pattern may comprise z-directional deflections. The methods may also comprise placing a plurality of absorbent foam particulates onto the carrier substrate, forming a loaded carrier substrate. The methods may further comprise providing a particulate settling means enabled to affect the loaded carrier substrate, affecting the loaded carrier substrate, forming a settled carrier substrate. The methods may further comprise associating a cover with the settled carrier substrate, forming a composite structure.

11 Claims, 7 Drawing Sheets

(51) Int. Cl.
    *A61F 13/534* (2006.01)
    *A61F 13/535* (2006.01)
    *A61F 13/15* (2006.01)
    *B32B 5/18* (2006.01)
    *B32B 5/24* (2006.01)
    *B32B 5/16* (2006.01)
    *B32B 7/12* (2006.01)
    *B32B 37/12* (2006.01)
    *B32B 5/02* (2006.01)
    *B32B 5/08* (2006.01)
    *B32B 5/22* (2006.01)
    *B32B 5/26* (2006.01)
    *B32B 5/32* (2006.01)
    *B32B 7/08* (2006.01)
    *B32B 27/06* (2006.01)
    *B32B 27/08* (2006.01)
    *B32B 27/10* (2006.01)
    *B32B 27/12* (2006.01)
    *B32B 27/32* (2006.01)
    *B32B 29/00* (2006.01)
    *B32B 29/02* (2006.01)
    *B32B 38/00* (2006.01)

(52) U.S. Cl.
    CPC .... *A61F 13/5323* (2013.01); *A61F 13/53436* (2013.01); *B32B 5/022* (2013.01); *B32B 5/024* (2013.01); *B32B 5/08* (2013.01); *B32B 5/16* (2013.01); *B32B 5/18* (2013.01); *B32B 5/22* (2013.01); *B32B 5/245* (2013.01); *B32B 5/26* (2013.01); *B32B 5/32* (2013.01); *B32B 7/08* (2013.01); *B32B 7/12* (2013.01); *B32B 27/065* (2013.01); *B32B 27/08* (2013.01); *B32B 27/10* (2013.01); *B32B 27/12* (2013.01); *B32B 27/32* (2013.01); *B32B 29/005* (2013.01); *B32B 29/007* (2013.01); *B32B 29/02* (2013.01); *B32B 37/12* (2013.01); *B32B 38/1875* (2013.01); *B32B 37/1284* (2013.01); *B32B 2255/02* (2013.01); *B32B 2262/02* (2013.01); *B32B 2262/0253* (2013.01); *B32B 2262/0276* (2013.01); *B32B 2262/06* (2013.01); *B32B 2262/062* (2013.01); *B32B 2262/067* (2013.01); *B32B 2262/12* (2013.01); *B32B 2262/14* (2013.01); *B32B 2264/025* (2013.01); *B32B 2266/0278* (2013.01); *B32B 2305/30* (2013.01); *B32B 2307/726* (2013.01); *B32B 2555/00* (2013.01)

(58) Field of Classification Search
    CPC .......... B32B 2262/067; B32B 2262/12; B32B 2262/14; B32B 2264/025; B32B 2266/0278; B32B 5/022; B32B 5/024; B32B 5/08; B32B 5/22; B32B 5/26; B32B 5/32; B32B 7/08; B32B 27/065; B32B 27/08; B32B 27/10; B32B 5/18; B32B 5/245; B32B 37/1284; B32B 38/1875; B32B 2305/30; B32B 5/16
    See application file for complete search history.

(56) References Cited

U.S. PATENT DOCUMENTS

| | | |
|---|---|---|
| 5,583,162 A | 12/1996 | Li et al. |
| 5,653,922 A | 8/1997 | Li et al. |
| 5,741,581 A | 4/1998 | DesMarais et al. |
| 5,858,292 A | 1/1999 | Dragoo et al. |
| 5,863,957 A | 1/1999 | Li et al. |
| 6,410,820 B1 | 6/2002 | McFall et al. |
| 6,582,411 B1 | 6/2003 | Carstens |
| 2002/0123283 A1 | 9/2002 | Dyer et al. |
| 2012/0308780 A1* | 12/2012 | Rottger ............ A61F 13/15658 428/172 |
| 2013/0006205 A1* | 1/2013 | McKiernan ........... A61L 15/20 604/366 |
| 2014/0296817 A1 | 10/2014 | Van Malderen |
| 2014/0303582 A1* | 10/2014 | Wright ................. A61F 13/539 604/365 |

* cited by examiner

METHOD FOR PRODUCING COMPOSITE STRUCTURES WITH A PLURALITY OF ABSORBENT FOAM PARTICULATES

FIELD OF THE INVENTION

The disclosed methods relate generally to methods for producing composite structures with a plurality of absorbent foam particulates.

BACKGROUND OF THE INVENTION

The manufacturing of certain composite structures to be used within absorbent articles often uses absorbent foam. The type of absorbent foam material may be chosen due to its specific properties. Absorbent foams may include latex polymer foams, polyurethane foams, and foams created by polymerizing an emulsion. One type of absorbent foam may be created from an emulsion that may be a dispersion of one liquid in another liquid and generally may be in the form of a water-in-oil mixture having an aqueous or water phase dispersed within a substantially immiscible continuous oil phase. These water-in-oil (or oil-in-water) emulsions have a high ratio of dispersed phase to continuous phase known in the art as High Internal Phase Emulsions, also referred to as "HIPE" or HIPEs. HIPE may be polymerized in either a continuous sheet or in a tubular reaction. Either process requires that one must use the polymerized open celled foam in a continuous sheet form or break up the polymerized open celled foam to make open celled foam pieces.

However, the conversion into a core presents a unique challenge. Prior uses have relied on using the sheet form or grinding the sheet form after being placed in a core to create particulates. This may be done so that one does not have to handle the foam in particulate form. These processes may be traditionally slow or tedious and may not be done at a rate that allows for high speed manufacturing. More specifically, it may be difficult to handle the foam particulates due to the triboelectric effect exhibited by dry foam particulates and due to how lightweight the particulates are.

Therefore, there exists a need for a process to place the foam particulates into or onto another material in a manner that allows for controllability of the foam particulates and for high speed processing, which is required for commercial output of absorbent articles. Further, there exists a need for a method to more effectively deliver foam particulates to a substrate.

SUMMARY OF THE INVENTION

A method that addresses the above need by providing a carrier substrate. The carrier substrate may comprise a pre-determined pattern. The pre-determined pattern may comprise z-directional deflections. The method may further comprise placing a plurality of absorbent foam particulates onto the carrier substrate, forming a loaded carrier substrate. The method may further comprise settling the loaded carrier substrate, forming a settled carrier substrate.

A method for producing composite structures with a plurality of absorbent foam particulates between substrates, wherein the method includes providing a carrier substrate. The carrier substrate may comprise a pre-determined pattern. The pre-determined pattern may comprise z-directional deflections. The method may further comprise providing a plurality of High Internal Phase Emulsion (HIPE) foam particulates. The method may further comprise placing the plurality of HIPE foam particulates onto the carrier substrate, forming a loaded carrier substrate. The method may further comprise settling the loaded carrier substrate, forming a settled carrier substrate.

An absorbent article comprising a composite structure wherein the composite structure is made by a method that includes providing a carrier substrate under tension, wherein the carrier substrate comprises a pre-determined pattern, wherein the pre-determined pattern comprises z-directional deflections. The method further includes providing a plurality of High Internal Phase Emulsion (HIPE) foam particulates. The method further includes placing the plurality of HIPE foam particulates onto the carrier substrate at a first location, forming a loaded carrier substrate. The method further includes settling the loaded carrier web such that at least one of the HIPE foam particulates changes location from the first location to a second location and associating a cover substrate with the settled carrier substrate to form a composite structure.

BRIEF DESCRIPTION OF THE DRAWINGS

While the specification concludes with claims particularly pointing out and distinctly claiming the subject matter of the disclosed methods, it is believed that the disclosed methods may be more readily understood from the following description taken in connection with the accompanying drawings, in which:

DETAILED DESCRIPTION OF THE INVENTION

Figure 1:
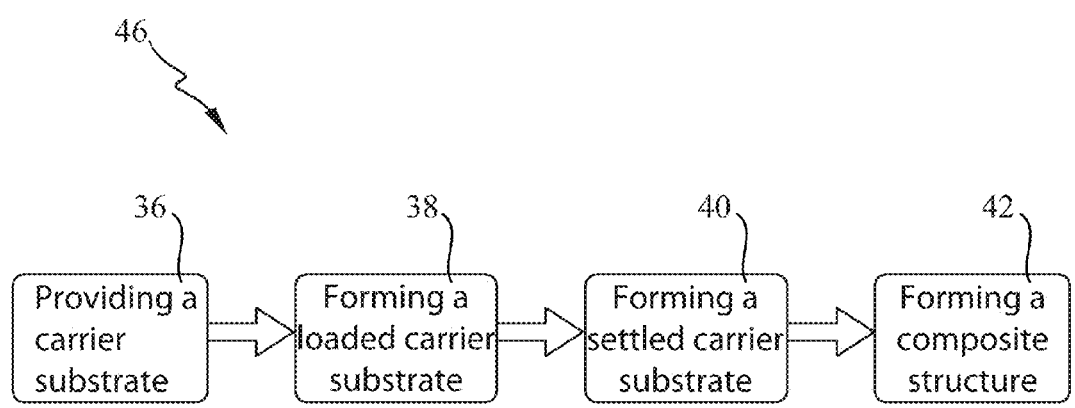
FIG. 1 is a simplified flowchart representation of the disclosed methods.

The following definitions may be useful in understanding the disclosed methods.

"Amplitude" refers herein to the peak-to-peak difference between the highest position and the lowest position of the surface of the vibration source when this surface is arranged horizontally and vibrates vertically.

"Associated" as used herein describes that the first item may be connected with something else. Association may occur due to entanglement, enrobing, direct contact, linking, connection, adhesion, or mechanical connection.

"Average weight" refers herein to the measurement of the mean particulate size multiplied by the skeletal density measured in milligrams.

"Cross direction" (CD) refers herein to a direction that is not parallel with, and is usually perpendicular to, the machine direction.

"Machine direction" (MD) refers herein to the direction of material flow through a process. In addition, relative placement and movement of material may be described as flowing in the machine direction through a process from upstream in the process to downstream in the process.

"Moisture content" refers herein to the percent of moisture within the individual particulate, given by the formula $M_{water}/(M_{water}+M_{polymer})$, where $M_{water}$ is the mass of the water content in an individual particulate, and $M_{polymer}$ is the mass of an individual particulate.

"Nonwoven web" refers herein to a web having a structure of individual fibers or threads which are interlaid, but not in a repeating pattern as in a woven or knitted fabric, which do not typically have randomly oriented fibers.

"Pattern" refers herein to a surface with protrusions or depressions thereon. The pre-determined pattern used in the disclosed methods is not limited to those having regular or repeating patterns thereon.

"Skeletal density" refers herein to the measurement of a combined mass of a certain number of particulates divided by the sum of the volume of these particulates, measured in grams per cubic centimeters.

The disclosed methods relate to forming composite structures with a plurality of absorbent foam particulates between substrates. More particularly, the methods are directed to placing absorbent foam particulates onto a carrier substrate, settling the absorbent foam particulates, and associating the carrier substrate with a cover substrate to form a composite structure. As discussed in more detail below, the methods may include adding moisture to the absorbent foam particulates. The addition of moisture to absorbent foam particulates may lessen or even neutralize the triboelectric effect, allowing for greater controllability over the handling of the absorbent foam particulates. Further to the above, the methods may include using a particulate settling means to settle the absorbent foam particulates on the carrier substrate. The particulate settling means may be a vibration source using vibrational frequency to relocate the absorbent foam particulates to desired areas. Further to the above, the carrier substrate may be associated with a cover substrate. The association of the two substrates may be where one of the two substrates is placed under tension. Placing one of the two substrates under tension eliminates the need for a supporting structure within the tensioning system. As discussed in more detail below, the methods according to the present disclosure may be utilized in the production of composite structures to place within absorbent articles, such as sanitary napkins.

FIG. 1 is a simplified flowchart representation of some embodiments of the disclosed methods 46. The methods 46 may include the step of providing a carrier substrate 36. The methods 46 may further include the step of forming a loaded carrier substrate 38. The methods 46 may further include the step of forming a settled carrier substrate 40. The methods 46 may further include the step of forming a composite structure 42. These steps are described in further detail herein with references to FIGS. 2-3.

Figure 2:
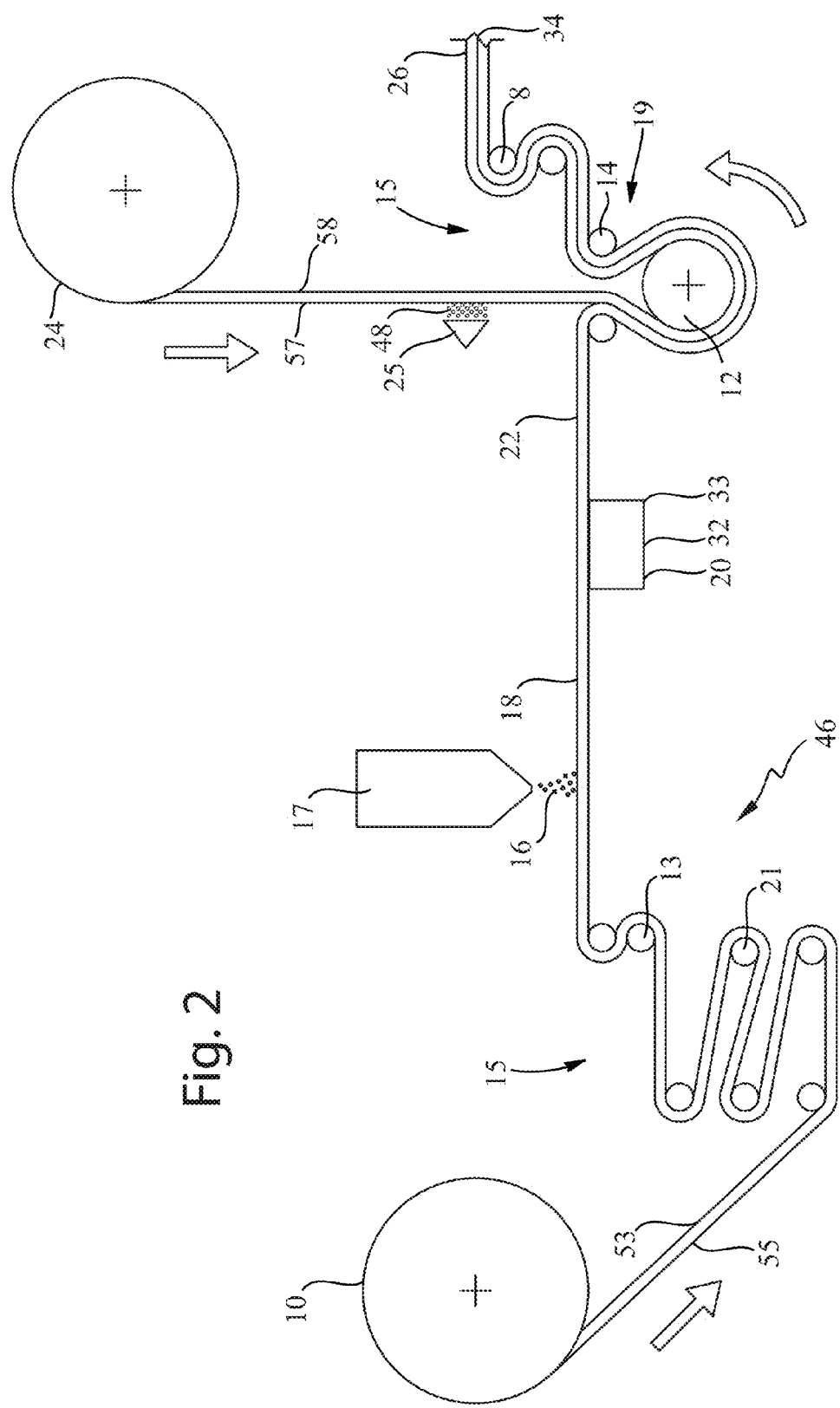
FIG. 2 is a schematic representation of some embodiments of the process of the disclosed methods.

FIG. 2 is a schematic representation of an example embodiment of the methods 46. The methods 46 may include providing a carrier substrate 10 having a carrier substrate first surface 53 and a carrier substrate second surface 55. The carrier substrate 10 may be transferred through a first portion of a substrate tensioning system 15. The first portion of the substrate tensioning system 15 may include supply roll control means 21 and metering means 13. A particulate delivery means 17 may place a plurality of absorbent foam particulates 16 on the carrier substrate first surface 53, forming a loaded carrier substrate 18. A particulate settling means 20 may affect the carrier substrate second surface 55 of the loaded carrier substrate 18, forming a settled carrier substrate 22. In an embodiment, at least one of the HIPE foam particulates will move from the location it was provided onto the carrier web or a first location to a second location on the carrier web when affected by the particulate settling means 20. The methods 46 may include providing a cover substrate 24 having a cover substrate first surface 58 and a cover substrate second surface 57. The cover substrate 24 and the settled carrier substrate 22 may be associated, forming a composite structure 26. To form the composite structure 26, an adhesive provider 25 may place an adhesive source 48 on the cover substrate second surface 57. The cover substrate second surface 57 may come together with the carrier substrate first surface 53 of the settled carrier substrate 22 and may be transferred through a composite forming system 19 and through a second portion of the substrate tensioning system 15. The composite forming system 19 may include composite forming components 12 and guiding means 14. The second portion of the substrate tensioning system 15 may include composite forming components 12 and a downstream tensioner 8.

The carrier substrate 10 may be manufactured from a wide range of materials such as woven and nonwoven webs; polymeric materials such as unapertured formed thermoplastic films, unapertured plastic films, and hydroformed thermoplastic films; porous foams; polyurethane foams; reticulated foams; reticulated thermoplastic films; paper webs; and thermoplastic scrims.

The carrier substrate 10 may be made in part from fibrous webs. The webs may be comprised of natural fibers (e.g., wood or cotton fibers), synthetic fibers (e.g., polymeric fibers such as polyester, polypropylene, or polyethylene fibers); bicomponent fibers (that is, fibers having a core of one material which may be enclosed in a sheath made of another material); shaped fibers, or from a combination of natural and synthetic fibers. Bicomponent fibers may be polypropylene (PP) and polyethylene (PE) in known configurations, including core/sheath, side by side, islands in the sea, or pie. Shaped fibers may be tri-lobal, H-shaped in cross section, or any other known cross-sectional shape.

The carrier substrate 10 may be made in part from a nonwoven web. Suitable nonwoven webs may include, but are not limited to: carded nonwovens; spunlaced nonwovens; spunbonded nonwovens; air laid nonwovens, including thermally bonded air laid nonwoven webs, latex bonded air laid nonwoven webs, and multi-bonded air laid nonwoven webs; and thermally bonded wet laid nonwoven webs.

One spunbonded nonwoven material may be a 19 g/yd.sup.2 (22.5 g/m$^2$) spunbonded polypropylene nonwoven material referred to as product No. 065MLPV60U (or "P-9") obtained from Fiberweb, North America of Washougal, Wash. Another nonwoven material may be a spunbonded polyethylene nonwoven material known as COROLIND sold by Corovin GmbH Peine, Germany which may be obtained in two basis weights, 23 gsm and 30 gsm.

Suitable thermally bonded air laid material (which may be referred to as "TBAL" for brevity) for use as a carrier substrate 10 may be fabricated from a blend of cellulose and synthetic fibers. Preferred thermally bonded air laid materials are described in U.S. Pat. No. 5,607,414 entitled, "Catamenial Absorbent Structures Having Thermally Bonded Layers for Improved Handling of Menstrual Fluids, and Their Use in Sanitary Napkins Having Improved Fit and Comfort" issued to Richards, et al. on Mar. 4, 1997.

One suitable low density latex bonded air laid material (which may be referred to as "LBAL" for brevity) for use as a carrier substrate 10 may be a material having a basis weight of about 80 g/m$^2$ known as product No. F6413MHB, which may be obtained from Walkisoft, USA of Mt. Holly, N.C.

A suitable multi-bonded air laid nonwoven material (which may be referred to as "MBAL" for brevity) may comprise about 77% cellulose fibers, about 20% powder binder, and about 3% latex binder (1.5% sprayed on each side of the substrate) and may have a basis weight of about 50 g/yd$^2$ (about 60 g/m.sup.2). (Unless otherwise stated, all percentages herein are by weight.) Such a multi-bonded air laid nonwoven may be obtained as product No. 90830X312 from Merfin Hygienic Products, Ltd. of Delta, British Columbia, Canada.

Suitable thermally bonded wet laid nonwoven webs (which may be referred to as "TBOWL" for brevity) are described in U.S. Pat. No. 5,549,589 entitled "Fluid Distribution Member for Absorbent Articles Exhibiting High Suction and High Capacity" issued to Homey, et al. on Aug. 27, 1996.

The carrier substrate 10 may be made in part from a microporous film, a formed film, or any other polymer film that may be fluid permeable, or rendered to be fluid permeable. The carrier substrate 10 may also be a fluid permeable polymer film with z-directional deflections, such as a z-directional deflection three-dimensional formed film as may be known in sanitary napkins such as ALWAYS® brand sanitary napkins.

The carrier substrate 10 may be fluid permeable if the carrier substrate 10 serves as a cover or topsheet, or as a backsheet for the absorbent article 34. The pores or openings in the carrier substrate 10 may be smaller than the absorbent foam particulates 16 for containment of the absorbent foam particulates 16 within the composite structure 26.

The carrier substrate 10 may also be a material that may be extensible, or stretchable prior to any mechanical manipulation thereof, if desired. For example, the carrier substrate 10 may be a film made of a polyethylene/Kraton blend such as the Exxon film formerly known as EXX-7, available from the Exxon Corporation. Additional extensible materials that are suitable for use as the carrier substrate 10 are described in U.S. Pat. No. 5,611,790 issued to Osborn.

One film that may be useful as material for the carrier substrate 10 may be a formed film described in one or more of the above patents and marketed on sanitary napkins by The Procter & Gamble Company of Cincinnati, Ohio as the "DRI-WEAVE" topsheet.

Suitable films for use are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991.

Figure 4:
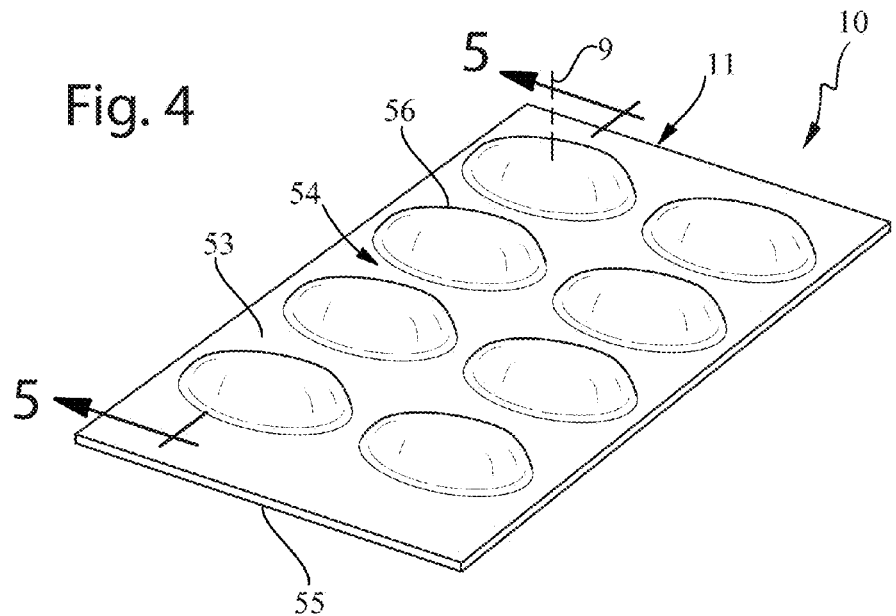
FIG. 4 is a schematic representation of a portion of a substrate after it has passed through a SELF process.

The carrier substrate 10 may include a pre-determined pattern 11, as further illustrated with reference to FIG. 4. The pre-determined pattern 11 may be formed onto the carrier substrate 10 using methods such as SELFing, rotary knife apparatus (RKA), or others, such as those described in co-owned U.S. Pat. No. 8,502,013, issued to Zhao, et al. on Aug. 6, 2013; U.S. Pat. No. 7,935,207, issued to Zhao, et al. on May 3, 2011; and U.S. Pat. No. 20080221539, issued to Zhao, et al. on Sep. 11, 2008. A substrate that has undergone the SELFing process is illustrated in FIG. 4. The pre-determined pattern 11 may be formed onto the substrate using the methods and equipment described in U.S. Pat. No. 5,916,661, issued to Benson; U.S. Pat. No. 5,628,097, issued to Benson; U.S. Pat. No. 8,679,391, issued to O'Donnell; U.S. Pat. No. 8,241,543, issued to O'Donnell; U.S. Pat. No. 5,650,214, issued to Anderson; U.S. Pat. No. 7,838,099, issued to Curro; U.S. Pat. No. 7,682,686, issued to Curro. The pre-determined pattern 11 may be formed onto the substrate using the methods and equipment described in U.S. Patent Application No. 62/049,376 filed on Sep. 12, 2014. A patterned substrate may include z-directional deflections 9, forming valleys 54 and peaks 56.

The carrier substrate 10 may be transferred through a first portion of a substrate tensioning system 15. A substrate tensioning system 15 may include, but is not limited to, a first portion and a second portion. The first portion and the second portion may be used in conjunction with each other. The first portion of the substrate tensioning system 15 may include, but is not limited to, supply roll control means 21 and metering means 13. The second portion of the substrate tensioning system 15 may include, but is not limited to, composite forming components 12 and a downstream tensioner 8, as described hereinafter. The supply roll control means 21 may include, but is not limited to, one or more dancers, load cells, or any other suitable means of controlling the supply roll known to one skilled in the art. The supply roll control means 21 may act to control the carrier substrate 10 by stabilizing the mass flow rate of the carrier substrate 10. The supply roll control means 21 in FIG. 2 illustrates dancers. The metering means 13 may include, but is not limited to, one or more s-wraps, omega rolls, driven rolls, vacuum conveyors, two rolls with a nip, or any other suitable means of providing tension known to one skilled in the art. The metering means 13 may act to ensure a constant and pre-determined amount of substrate tension upstream in the methods 46. The metering means 13 in FIG. 2 illustrates an s-wrap.

The tension system 15 may comprise a tension range of between about 0.1 pounds per linear inch (pli) and about 1.0 pli, such as for example, 0.15 pli, 0.2 pli, 0.25 pli, 0.3 pli, 0.35 pli, 0.4 pli, 0.45 pli, 0.5 pli, 0.55 pli, 0.6 pli, 0.65 pli, 0.7 pli, 0.75 pli, 0.8 pli, 0.85 pli, 0.9 pli, and 0.95 pli. The tension system 15 may comprise a tension range of between about 0.3 pli and 0.6 pli.

A particulate delivery means 17 may place a plurality of absorbent foam particulates 16 in situ on the carrier substrate first surface 53, forming a loaded carrier substrate 18. The particulate delivery means 17 may be, but is not limited to, a gravity feeder, a drum, a shaker, an auger feed, a rotary valve feeder, a belt feeder, a screw feeder, a vibratory feeder, or any other suitable delivery means known to one skilled in the art. The auger feed may or may not utilize additional vibration means. The particulate delivery means 17 may place the plurality of absorbent foam particulates 16 onto the carrier substrate first surface 53 at a constant rate. The constant rate may be set by the user, by synchronizing the rate at which the carrier substrate 10 moves in the machine direction (MD).

The loaded carrier substrate 18 is further illustrated with reference to FIG. 5A. The particulate delivery means 17 may place the plurality of absorbent foam particulates 16 on the carrier substrate first surface 53 in a patterned fashion, in individual lines, or in any other form known to one skilled in the art. The particulate delivery means 17 may place the plurality of absorbent foam particulates 16 in a pre-determined width across the cross direction (CD) of the carrier substrate 10. The pre-determined width may be the usable area of the SELFed carrier substrate 10.

The plurality of absorbent foam particulates 16 may comprise any suitable absorbent foam known to one skilled in the art, such as for example, High Internal Phase Emulsion (HIPE) foam and polyurethane. The plurality of absorbent foam particulates 16 may comprise more than one type of foam. For example, some of the absorbent foam particulates 16 may be polymerized HIPE while other absorbent foam particulates 16 may be made from polyurethane. The different absorbent foam particulates 16 may be located at specific locations within the composite structure 26 based on their properties to optimize performance.

In some embodiments, open celled foam may be a thermoset polymeric foam made from the polymerization of a High Internal Phase Emulsion (HIPE), also referred to as a polyHIPE. To form a HIPE, an aqueous phase and an oil phase are combined in a ratio between about 8:1 and 200:1. In certain embodiments, the aqueous phase to oil phase ratio may be between about 10:1 and about 120:1, and in certain other embodiments the aqueous phase to oil phase ratio may be between about 20:1 and about 80:1. This is termed the "water-to-oil" or W:O ratio and may be used to determine the density of the resulting polyHIPE foam. As discussed, the oil phase may contain one or more of monomers, comonomers, crosslinkers, and emulsifiers, as well as optional components. The water phase will contain water and in certain embodiments one or more components such as electrolytes, initiators, or optional components.

The open cell foam may be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, and in certain embodiments, after the HIPE has been formed. The emulsion making process may produce a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE may be withdrawn or pumped from the mixing zone. One method for forming HIPEs using a continuous process is described in U.S. Pat. No. 5,149,720, issued to DesMarais, et al. on Sep. 22, 1992; U.S. Pat. No. 5,827,909, issued to DesMarais, et al. on Oct. 27, 1998; and U.S. Pat. No. 6,369,121, issued to Catalfamo et al. on Apr. 9, 2002.

In some embodiments, open cell foam may be produced from the polymerization of the monomers having a continuous oil phase of a High Internal Phase Emulsion (HIPE). The HIPE may have two phases. One phase may be a continuous oil phase having monomers that are polymerized to form a HIPE foam and an emulsifier to help stabilize the HIPE. The monomer(s) component may be present in an amount of from about 80% to about 99%, and in certain embodiments from about 85% to about 95% by weight of the oil phase. The emulsifier component, which may be soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers may include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, may be added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Additional substantially water-insoluble comonomer(s) may be added to the oil phase in weight percentages of from about 0% to about 25% by weight of the oil phase, in certain embodiments from about 1% to about 10%, to modify properties of the HIPE foams. In certain embodiments, "toughening" monomers may be desired which impart toughness to the resulting HIPE foam. These may include monomers such as styrene, vinyl chloride, vinylidene chloride, isoprene, and chloroprene. Without wishing to be bound by theory, it may be believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028, issued to Dyer on Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers may be used to slow down the polymerization rate of a HIPE. Examples of monomers of this type may have styrene and vinyl chloride.

The oil phase may further contain an emulsifier used for stabilizing the HIPE. Emulsifiers used in a HIPE may include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207, issued to Dyer, et al. on Feb. 7, 1995 and U.S. Pat. No. 5,500,451, issued to Goldman, et al. on Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they may have between about 1% and about 20%, in certain embodiments from about 2% to about 15%, and in certain other embodiments from about 3% to about 12% by weight of the oil phase. In certain embodiments, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. In certain embodiments, ditallow dimethyl ammonium methyl sulfate (DTDMAMS) may be used as a coemulsifier.

The dispersed aqueous phase of a HIPE may have water, and may also have one or more components, such as initiator, or electrolyte, wherein in certain embodiments, one or more components may be at least partially water soluble.

In addition to the previously described components, other components may be included in either the aqueous or oil phase of a HIPE. Examples include antioxidants, for example hindered phenolics, hindered amine light stabilizers; inhibitors, for example 4 methoxy phenone, plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The size of each individual particulate of the plurality of absorbent foam particulates 16 may be such that each individual particulate fits within the width of the valley 54, as illustrated in FIGS. 4-7. The size of each individual particulate of the plurality of absorbent foam particulates 16 may be the width of the valley 54, as illustrated in FIGS. 4-7. The size of each individual particulate of the plurality of absorbent foam particulates 16 may be 20% larger than the width of the valley 54, as illustrated in FIGS. 4-7.

The absorbent foam particulates 16 may be of any shape that allows for the absorption of fluid. The absorbent foam particulates 16 may be of regular shapes. The absorbent foam particulates 16 may be of irregular shapes. Examples of regular shapes may include but are not limited to cubes, three dimensional rectangles, prisms, or other parallelepipeds. Examples of irregular shapes may include but are not limited to space rock configurations, gravel configurations, and any other irregular shapes. The individual particulates of the absorbent foam particulates 16 may all be of the same general size and general shape, or the individual particulates of the absorbent foam particulates 16 may be of varying sizes and shapes. When the individual particulates of the absorbent foam particulates 16 are described as being of the same "general" size and shape, it is understood that the individual particulates of the absorbent foam particulates 16 need not be exactly of the same shape or size specified, and that all of the individual particulates of the absorbent foam particulates 16 need not be exactly in the shape or size specified.

The absorbent foam particulates 16 may have a skeletal density of about 0.1 g/cm$^3$ and about 2.0 g/cm$^3$, such as for example, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.9 g/cm$^3$, 1.0 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, and 1.9 g/cm$^3$. For instance, dependent upon the chemical composition, the absorbent foam particulates 16 may have a skeletal density of between about 0.9 g/cm$^3$ and about 1.1 g/cm$^3$.

The absorbent foam particulates 16 may have an average particulate weight of about 0.1 mg to about 2.0 mg, such as for example, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, and 1.9 mg. For instance, dependent upon the chemical composition, the absorbent foam particulates 16 may have an average particulate weight of between about 0.5 mg and about 1.5 mg.

Without wishing to be bound by theory, applicants have found that the processing of the materials may be eased when there the plurality of absorbent foam particulates 16 contain a certain moisture content. The moisture content works to reduce the triboelectric effect, or static electricity, which typically affects the handling of the lightweight plurality of absorbent foam particulates 16. Dry particulates, in particular HIPE foam particulates, may contain an electrostatic charge. Because such particulates are dry, such particulates are insulative, or preventative of the passage of electricity into or out of these dry particulates. Dry particulates thus cannot dissipate their electrostatic charges because all the surrounding particulates are also insulative. Because dry particulates maintain these charges, these dry particulates either repel one another or attract one another, depending upon the particulates' polarities. This repulsion or attraction makes dry particulates difficult to control the relocation of, because the electrostatic charges may cause the particulates to move in unpredictable ways.

When moisture is added to dry particulates, the particulates become conductive, allowing for the electrostatic charges to flow through the particulates eventually to the ground, ridding the system of electrostatic charge. Once the particulates lose their electrostatic charge, the particulates will no longer repel one another or be attracted to one another. Without their electrostatic charge, there may be less of an interference in moving the particulates to the user's desired location. Moisture may be added to the absorbent foam particulates 16 prior to placement on the carrier substrate first surface 53.

The plurality of absorbent foam particulates 16 may comprise less than 99.9% moisture content. The plurality of absorbent foam particulates 16 may contain between about 8% and about 99.9% moisture content. The plurality of absorbent foam particulates 16 may contain between about 10% and about 95% moisture content, such as for example, 15%, 20%, 25%, 30%, 35%, 40%, 45%, 50%, 55%, 60%, 65%, 70%, 75%, 80%, 85%, and 90% moisture content. The plurality of absorbent foam particulates 16 may contain between about 50% and about 60% moisture content. The moisture content may be spread uniformly throughout the individual particulates of the absorbent foam particulates 16.

The particulate delivery means 17 may place the plurality of absorbent foam particulates 16 where some of the absorbent foam particulates 16 may fall on the peaks 56 of the carrier substrate first surface 53, as is further illustrated in FIG. 5A. The particulate delivery means 17 may place the plurality of absorbent foam particulates 16 where some of the absorbent foam particulates 16 may fall within the valleys 54 of the carrier substrate first surface 53, as is further illustrated in FIG. 5A.

A particulate settling means 20 may affect the carrier substrate second surface 55 of the loaded carrier substrate 18, forming a settled carrier substrate 22. In an embodiment, at least one of the HIPE foam particulates will move from the location it was provided onto the carrier web or a first location to a second location on the carrier web when affected by the particulate settling means 20. Without the particulate settling means 20, the absorbent foam particulates 16 may remain where initially placed on the carrier substrate first surface 53 due to some force, for example, a frictional force between the surface of the absorbent foam particulates 16 and the carrier substrate first surface 53. The particulate settling means 20 may enable the relocation of the absorbent foam particulates 16. The particulate settling means 20 may comprise a vibration source 32 or a vacuum 33. The vibration source 32 may be a vibrating plate or any other vibrating apparatus that may cause relocation of the absorbent foam particulates 16. The vibration source 32 may use gravity to relocate the plurality absorbent foam particulates 16.

The vibration source 32 may have a frequency and an amplitude. The frequency may aid in relocating the plurality of absorbent foam particulates 16 to desired areas of the carrier substrate first surface 53. Desired areas of the carrier substrate first surface 53 may be the valleys 54, as further illustrated in FIG. 5A. The vibration source 32 may have a frequency of between about 5 Hz to about 200 Hz, such as for example, 10 Hz, 15 Hz, 20 Hz, 25 Hz, 30 Hz, 35 Hz, 40 Hz, 45 Hz, 50 Hz, 55 Hz, 60 Hz, 65 Hz, 70 Hz, 75 Hz, 80 Hz, 85 Hz, 90 Hz, 95 Hz, 100 Hz, 105 Hz, 110 Hz, 115 Hz, 120 Hz, 125 Hz, 130 Hz, 135 Hz, 140 Hz, 145 Hz, 150 Hz, 155 Hz, 160 Hz, 165 Hz, 170 Hz, 175 Hz, 180 Hz, 185 Hz, 190 Hz, and 195 Hz. The vibration source 32 may have a frequency of between about 25 Hz and about 70 Hz. The frequency of the vibration source 32 may not be so high so that the absorbent foam particulates 16 are unable to travel due to higher inertia. The frequency of the vibration source 32 may not be so low that the absorbent foam particulates 16 are unable to jump vertically or horizontally and relocate into the desired areas of the carrier substrate first surface 53. The vibration source 32 may affect the carrier substrate second surface 55 of the loaded carrier substrate 18 for sufficient enough time to relocate the plurality of absorbent foam particulates 16 from a first location to the desired areas or a second location.

The amplitude may aid in relocating the plurality of absorbent foam particulates 16 to the aforementioned desired areas. The vibration source 32 may have an amplitude of between about 0.0 micron to about 1000 microns. The vibration source 32 may have an amplitude of between about 50 microns to about 200 microns, such as for example, 50 microns, 60 microns, 70 microns, 80 microns, 90 microns, 100 microns, 110 microns, 120 microns, 130 microns, 140 microns, 150 microns, 160 microns, 170 microns, 180 microns, and 190 microns. The vibration source 32 may have an amplitude of between about 80 microns and about 120 microns.

The particulate settling means 20 may be a vacuum 33. The vacuum 33 may be any suitable vacuum apparatus known to one skilled in the art. The vacuum 33 may create suction capable of pulling the absorbent foam particulates 16 downwards, towards the carrier substrate 10. The vacuum 33 may relocate the absorbent foam particulates 16 into the aforementioned desired areas.

It is to be appreciated that the particulate settling means 20 may be any combination of a vibration source 32, a vacuum 33, a doctor blade 30, a doctor brush 31, with reference to FIG. 3, or any other suitable means known to one skilled in the art.

A settled carrier substrate 22 may be formed when the peaks 56 of the carrier substrate 10 are substantially free of absorbent foam particulates 16, with reference to FIG. 5B. Substantially free may be where there remain few enough absorbent foam particulates 16 to enable the association of a cover substrate 24 with the settled carrier substrate 22. Substantially free may be where greater than 80% of the absorbent foam particulates 16 are within the valleys 54, with reference to FIG. 5B. Substantially free may be where up to 100% of the absorbent foam particulates 16 are within the valleys 54, with reference to FIG. 5B. The settled carrier substrate 22 is further illustrated with reference to FIG. 5B.

The methods 46 may include providing a cover substrate 24 having a cover substrate first surface 58 and a cover substrate second surface 57. The cover substrate 24 may comprise any of the materials listed above pertaining to the carrier substrate 10. The cover substrate 24 may be fluid permeable if the cover substrate 24 serves as a cover or topsheet, or as a backsheet for the absorbent article 34.

The cover substrate 24 and the settled carrier substrate 22 may be associated, forming a composite structure 26. To form the composite structure 26, an adhesive provider 25 may place an adhesive source 48 on the cover substrate second surface 57. The cover substrate second surface 57 may come together with the carrier substrate first surface 53 of the settled carrier substrate 22 and may be transferred through a composite forming system 19 and through a second portion of the substrate tensioning system 15.

The adhesive provider 25 may be a hot melt adhesive gun, a solvent-based adhesive nozzle, or any other suitable adhesive provider known to one skilled in the art. The adhesive source 48 may be hot melt adhesive, solvent based adhesive, or by any other suitable adhesive source known to one skilled in the art. The adhesive provider 25 may place the adhesive source 48 on the cover substrate second surface 57 in any suitable thickness that may not penetrate through the cover substrate 24. The adhesive provider 25 may place the adhesive source 48 onto the cover substrate second surface 57 where less than 100% of the cover substrate second surface 57 may contain the adhesive source 48. The adhesive provider 25 may place the adhesive source 48 onto the cover substrate second surface 57 where up to 100% of the cover substrate second surface 57 may contain the adhesive source 48. The adhesive provider 25 may place the adhesive source 48 onto the cover substrate second surface 57 in any known pattern such as, for example, a serpentine pattern, a square pattern, one or more circles, one or more lines, or any combinations thereof. Placement of the adhesive source 48 onto the cover substrate second surface 57 may create bonding points 52, as illustrated in FIGS. 6A-6C and 7A-7B.

The adhesive provider 25 may provide an adhesive source 48 onto both the cover substrate second surface 57 and to the carrier substrate first surface 53 of the settled carrier substrate 22.

It is to be understood that in lieu of an adhesive source 48 and an adhesive provider 25, Velcro may be used to associate the cover substrate 24 and the settled carrier substrate 22. In some embodiments, the carrier substrate first surface 53 and the cover substrate second surface 57 may be made of Velcro material. In some embodiments, the cover substrate second surface 57 may consist of a hook component and the carrier substrate first surface 53 may consist of a loop component. In some embodiments, the cover substrate second surface 57 may consist of a loop component and the carrier substrate first surface 53 may consist of a hook component. The hook component and the loop component may be of a smaller size than the size of the absorbent foam particulates 16 so that the absorbent foam particulates 16 may settle on top of the hook component and on top of the loop component, rather than fall within the hook component and/or within the loop component, which would make it more difficult for the Velcro components to associate with each other.

The composite forming system 19 may include, but is not limited to, composite forming components 12 and guiding means 14. The composite forming components 12 may include, but are not limited to one or more rolls, curved plates, turrets, drums, conveyors, Mt. Hope rolls, or any other suitable means of providing tension known to one skilled in the art. The composite forming components 12 may act to hold the settled carrier substrate 22 with the cover substrate 24 at a pre-determined amount of normal force for a pre-determined amount of time needed for association. The composite forming component 12 in FIG. 2 illustrates a roll. The guiding means 14 may include, but are not limited to, one or more rolls, idlers, rollers, stationary bars, or any other suitable means of providing guidance known to one skilled in the art. The guiding means 14 may act to associate the settled carrier substrate 22 and the cover substrate 24 together. The guiding means 14 may act to define a wrap angle of the settled carrier substrate 22 and the cover substrate 24 around the composite forming component 12. The guiding means 14 in FIG. 2 illustrates two rolls. The composite forming component 12 and the guiding means 14 may work in conjunction by placing the settled carrier substrate 22 under tension such that the settled carrier substrate 22 is forced to contact the cover substrate 24 which is in contact with the composite forming component 12.

The second portion of the substrate tensioning system 15 may include, but is not limited to, composite forming components 12 and a downstream tensioner 8. Composite forming components 12 may include any of the aforementioned components. A downstream tensioner 8 may include, but is not limited to, one or more s-wraps, omega rolls, driven rolls, vacuum conveyors, two rolls with a nip, or any other suitable means of providing downstream tension known to one skilled in the art. The downstream tensioner 8 may act to ensure a constant and pre-determined amount of substrate tension downstream in the methods 46. The downstream tensioner 8 in FIG. 2 illustrates an s-wrap.

Figure 3:
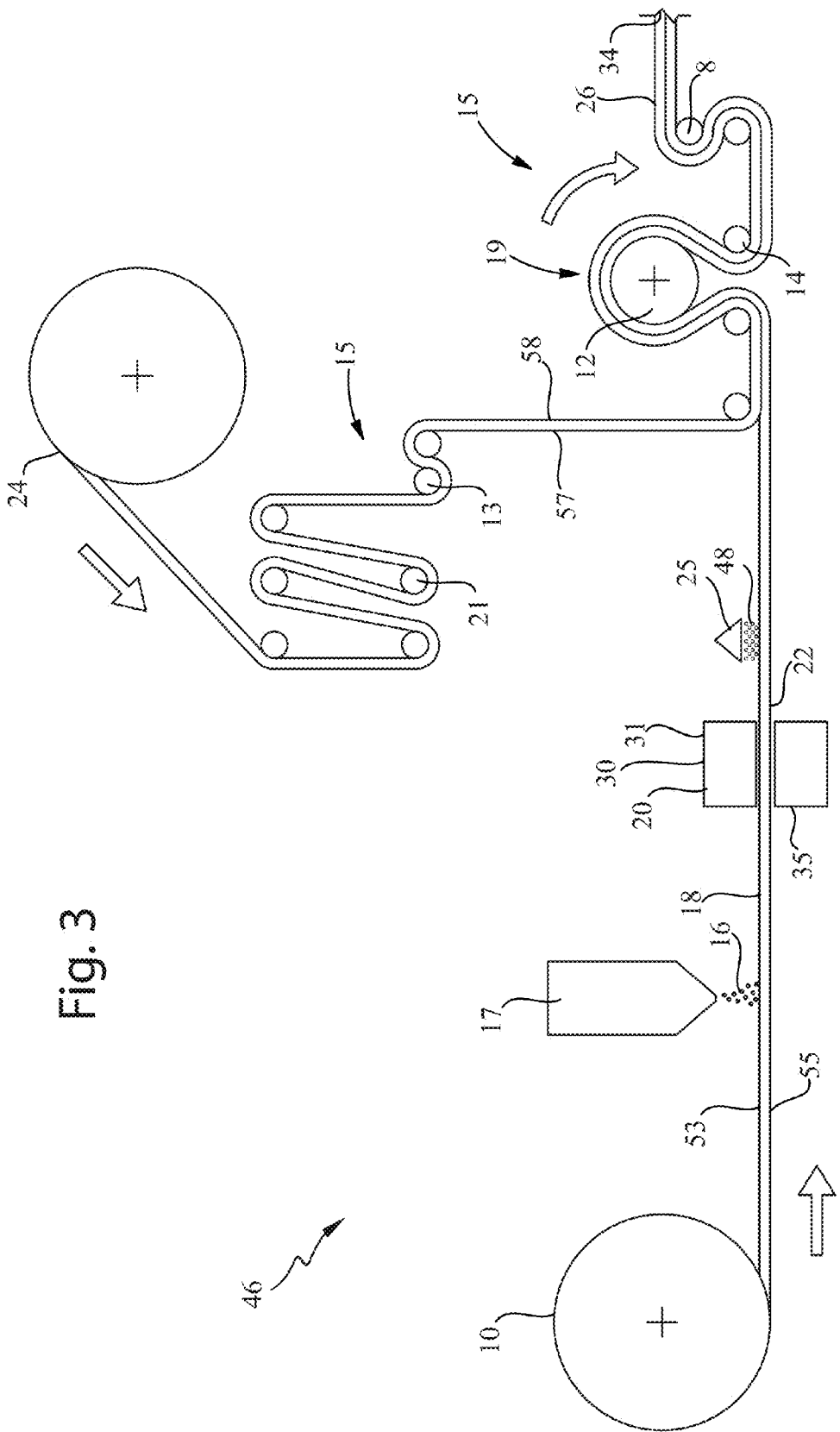
FIG. 3 is a schematic representation of an alternative embodiment of the process of the disclosed methods.

FIG. 3 is a schematic representation of an example embodiment of the methods 46 as described above with reference to FIG. 2. As shown in FIG. 3, the particulate settling means 20 may comprise a doctor blade 30 or a doctor brush 31. The doctor blade 30 may be any suitable doctor blade apparatus known to one skilled in the art. The doctor blade 30 may be run over the carrier substrate first surface 53 of the loaded carrier substrate 18 at a constant rate which may be set by the rate of the loaded carrier substrate 18 moving in the MD. The doctor blade 30 may relocate the absorbent foam particulates 16 into the aforementioned desired areas. The doctor blade 30 may use gravity to relocate the plurality of absorbent foam particulates 16. The doctor blade 30 may utilize a support plate 35. The support plate 35 may be located beneath the carrier substrate second surface 55. The support plate 35 may assist in keeping the doctor blade 30 level.

The doctor brush 31 may be any suitable doctor brush apparatus known to one skilled in the art. The doctor brush 31 may be run over the carrier substrate first surface 53 of the loaded carrier substrate 18 at a constant rate which may be set by the rate of the loaded carrier substrate 18 moving in the MD. The doctor brush 31 may relocate the absorbent foam particulates 16 into the aforementioned desired areas. The doctor brush 31 may use gravity to relocate the plurality of absorbent foam particulates 16 into the aforementioned desired areas. The doctor brush 31 may utilize a support plate 35. The support plate 35 may be located beneath the carrier substrate second surface 55. The support plate 35 may assist in keeping the doctor brush 31 level.

As shown in FIG. 3, an adhesive provider 25 may place an adhesive source 48 on the carrier substrate first surface 53 of the settled carrier substrate 22. Where there is adhesive source 48 present, the plurality of absorbent foam particulates 16 may be in the form of absorbent foam particulates 16 that are attached to the carrier substrate first surface 53. These attached absorbent foam particulates 16 may form band-like structures. Where there is no adhesive source 48 present, the plurality of absorbent foam particulates 16 will be in the form of "loose" particulates that are contained by the band-like structures formed by the attached particulates.

As shown in FIG. 3, the cover substrate 24 may be transferred through the first portion of the substrate tensioning system 15. The composite forming component 12 and the guiding means 14 may work in conjunction by placing the cover substrate 24 under tension such that the cover substrate 24 is forced to contact the settled carrier substrate 22 which is in contact with the composite forming component 12.

The composite structure 26 may be placed within an absorbent article 34. The composite structure 26 may be used as any part of an absorbent article 34 including, for example, as parts of an absorbent core, and/or as an absorbent core for an absorbent article 34. An absorbent article 34 may include, but is not limited to, sanitary napkins, panty liners, tampons, interlabial devices, wound dressings, diapers, adult incontinence articles, and the like, which are intended for the absorption of body fluids, such as menses or blood or vaginal discharges or urine. The composite structure 26 may be used in any product utilized to absorb and retain a fluid, including surface wipes. Exemplary absorbent articles 34 in the context of the disclosed methods 46 are disposable absorbent articles.

FIG. 4 is a schematic representation of a portion of a cross-section of a substrate after it has passed through a SELF process as discussed with reference to FIG. 2. The substrate shown may be of suitable material for use as the carrier substrate 10. The carrier substrate 10 may comprise a pre-determined pattern 11. The pre-determined pattern 11 may comprise z-directional deflections 9. The z-directional deflections 9 may protrude outward of the carrier substrate first surface 53. The z-directional deflections 9 may protrude inward of the carrier substrate second surface 55. The z-directional deflections 9 appear as upright structures. The z-directional deflections 9 may create areas of elevated substrate material, where the tops of the elevated substrate material may be peaks 56. The peaks 56 may be slightly curved. The peaks 56 may be slightly planar. The peaks 56 may be of any suitable angular configuration known to one skilled in the art. The z-directional deflections 9 may have substantially planar material in between the elevated substrate material which may be valleys 54. The valleys 54 may be of lower elevation than the elevated substrate material. The valleys 54 may be slightly recessed. The valleys 54 may be of any suitable width to collect absorbent foam particulates 16.

Figure 5A:
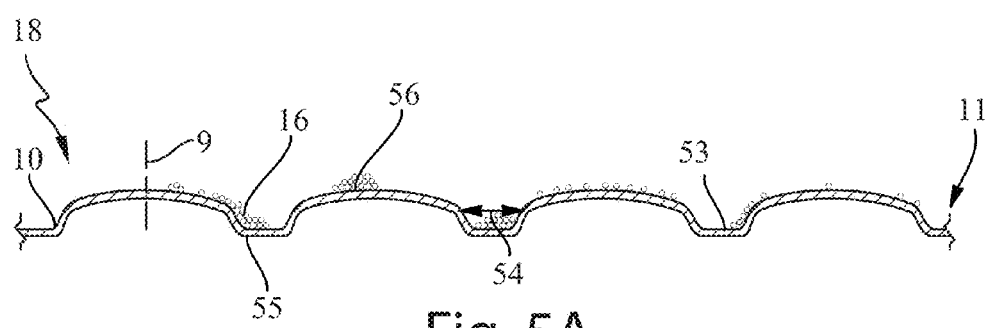
FIG. 5A is a schematic representation of the cross-section of a substrate after particulates have been placed on the substrate.
Figure 5B:
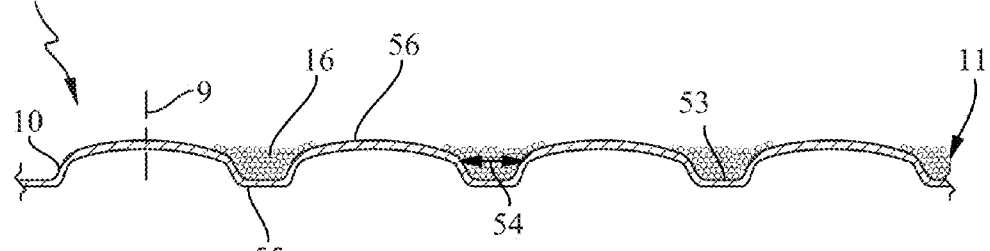
FIG. 5B is a schematic representation of the cross-section of a substrate after the particles have been settled.

FIG. 5A is a schematic representation of the cross-section of the carrier substrate 10 after absorbent foam particulates 16 have been placed on the carrier substrate first surface 53, forming a loaded carrier substrate 18. FIG. 5B is a schematic representation of FIG. 5A after a particulate settling means 20 has affected the loaded carrier substrate 18, forming a settled carrier substrate 22. The carrier substrate 10 may comprise a pre-determined pattern 11 as discussed previously with reference to FIG. 4. The pre-determined pattern 11 may comprise z-directional deflections 9 as discussed previously with reference to FIG. 4. The formed carrier substrate 10 may include peaks 56 and valleys 54 as previously described in FIG. 4. Absorbent foam particulates 16 may be placed on the carrier substrate first surface 53. The carrier substrate 10 may not have absorbent foam particulates 16 placed on the carrier substrate second surface 55. As shown in both FIGS. 5A-5B, the aforementioned elements are common to both representations.

FIG. 5A illustrates the loaded carrier substrate 18. The loaded carrier substrate 18 may contain absorbent foam particulates 16 placed randomly on the peaks 56 of the carrier substrate first surface 53. The loaded carrier substrate 18 may contain absorbent foam particulates 16 placed randomly within the valleys 54 of the carrier substrate first surface 53. The absorbent foam particulates 16 may be placed in any manner and spread as previously described with reference to FIG. 2.

FIG. 5B illustrates the settled carrier substrate 22. The settled carrier substrate 22 may contain absorbent foam particulates 16 that may have been relocated from the peaks 56 on the carrier substrate first surface 53 to the valleys 54 on the carrier substrate first surface 53. The absorbent foam particulates 16 may fill the entire width of the valleys 54. The absorbent foam particulates 16 may fill any portion of the width of the valleys 54. The absorbent foam particulates 16 may fill no portion of the width of the valleys 54. The peaks 56 may be substantially free of absorbent foam particulates 16. Substantially free may be where greater than 80% of the absorbent foam particulates 16 are within the valleys 54, as previously discussed with reference to FIG. 2. Substantially free may be where up to 100% of the absorbent foam particulates 16 are within the valleys 54, as previously discussed with reference to FIG. 2. The plurality of absorbent foam particulates 16 may be placed within the valleys 54 in any manner and spread as previously described with reference to FIG. 2.

Figure 6A:
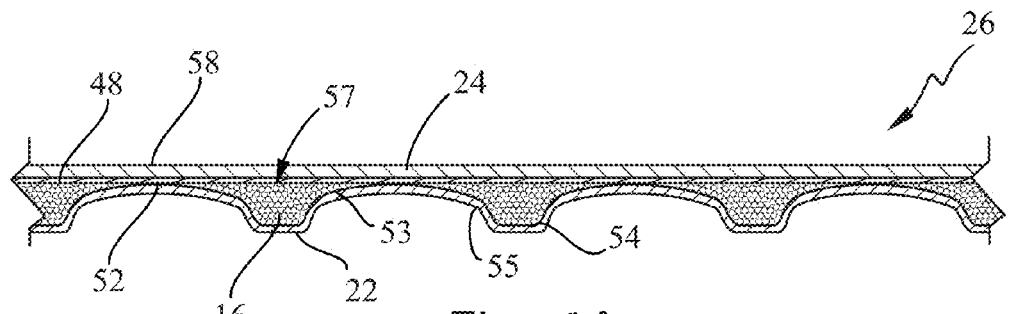
FIGS. 6A-6C are schematic representations of the cross-sections of alternative resulting composite structures.
Figure 6B:
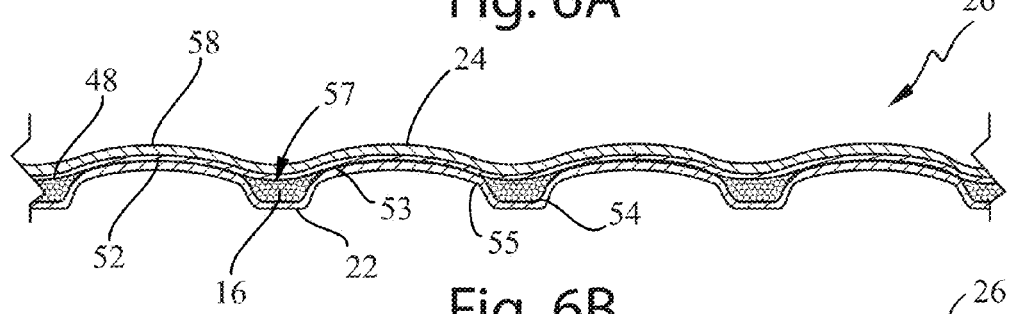
Figure 6C:
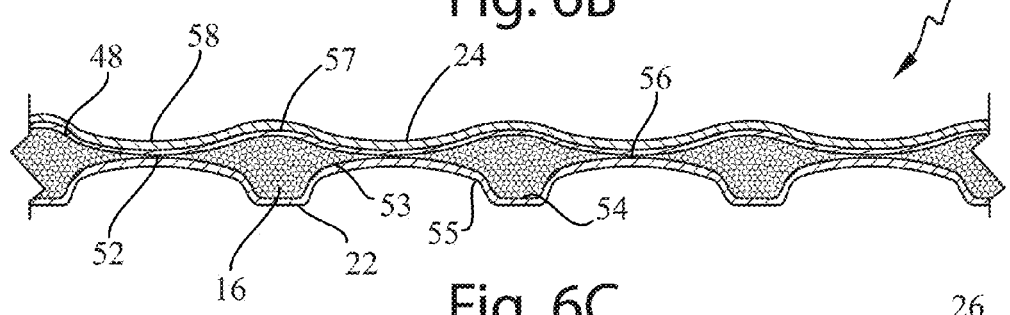
Figure 7A:
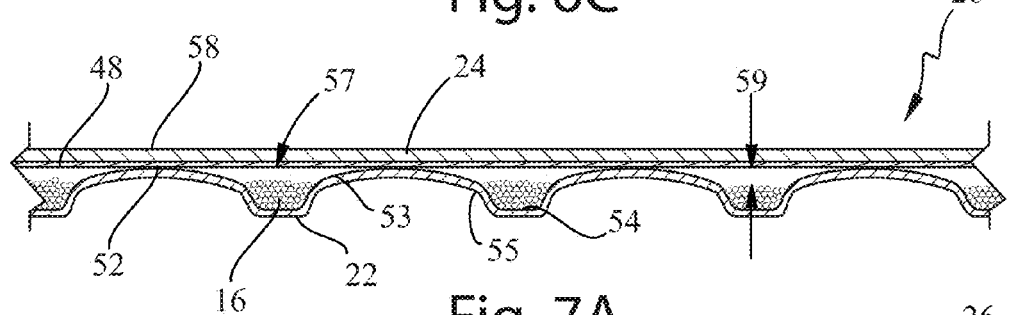
FIGS. 7A-7B are schematic representations of the cross-sections of the resulting composite structure of FIGS. 6A-6C, after passing through a drying means.
Figure 7B:
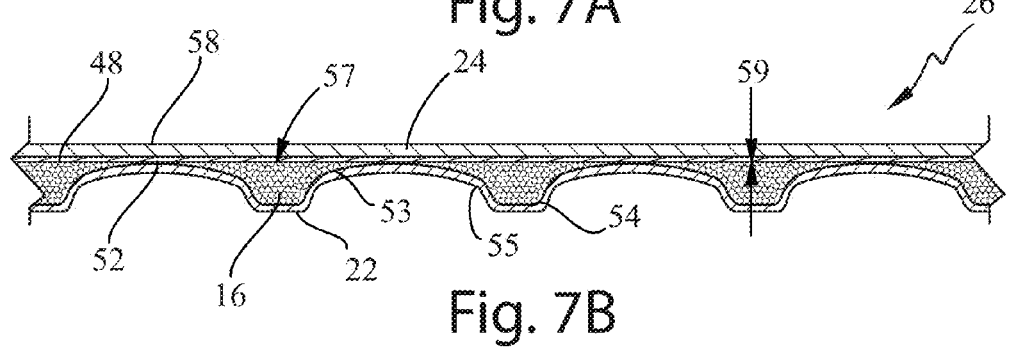

FIGS. 6A-6C are schematic representations of the cross-section of alternative resulting composite structures 26. FIGS. 7A-7B are schematic representations of the cross-section of the resulting composite structure 26 of FIGS. 6A-6C, after passing through a drying means.

The carrier substrate first surface 53 of the settled carrier substrate 22 may be associated with the cover substrate second surface 57 by an adhesive source 48. The adhesive source 48 may be placed on the cover substrate second surface 57 as previously described in FIG. 2. The adhesive source 48 may be placed on the carrier substrate first surface 53 of the settled carrier substrate 22, as previously described in FIG. 3. The adhesive source 48 may be placed on both the cover substrate second surface 57 and the carrier substrate first surface 53 of the settled carrier substrate 22. The adhesive source 48 may be of any suitable adhesive source 48 as described with reference to FIG. 2. Application of the adhesive source 48 may create bonding points 52. The bonding points 52 may be the sites where the carrier substrate first surface 53 of the settled carrier substrate 22 and the cover substrate second surface 57 associate. The peaks 56 may be substantially free of absorbent foam particulates 16, as previously described in FIG. 2. The valleys 54 may have absorbent foam particulates 16 placed within. Absorbent foam particulates 16 may not be placed on the carrier substrate second surface 55. Absorbent foam particulates 16 may not be placed on the cover substrate second surface 57. As shown in FIGS. 6A-6C and 7A-7B, the aforementioned elements are common all the aforementioned figures.

FIG. 6A illustrates a composite structure 26 where enough absorbent foam particulates 16 may be placed in the valleys 54 of the settled carrier substrate 22 so that when the cover substrate 24 may be associated with the settled carrier substrate 22, the cover substrate 24 remains relatively planar between the bonding points 52.

FIG. 6B illustrates a composite structure 26 where more absorbent foam particulates 16 may be placed in the valleys 54 of the settled carrier substrate 22 so that when the cover substrate 24 may be associated with the settled carrier substrate 22, the cover substrate 24 may be caused to become nonplanar such that portions of the cover substrate 24 deflect towards the valleys 54 of the settled carrier substrate 22. This may result in a smaller distance between the cover substrate 24 and the settled carrier substrate 22.

FIG. 6C illustrates a composite structure 26 where less absorbent foam particulates 16 may be placed in the valleys 54 of the settled carrier substrate 22 so that when the cover substrate 24 may be associated with the settled carrier substrate 22, the cover substrate 24 may be caused to become nonplanar such that portions of the cover substrate 24 deflect away from the valleys 54 of the settled carrier substrate 22. This may result in a larger distance between the cover substrate 24 and the settled carrier substrate 22.

The resulting composite structure 26 may comprise a combination of the different embodiments illustrated in FIGS. 6A-6C.

FIGS. 7A-7B illustrate resulting composite structures 26 after passing through a drying means. Drying may be accomplished by any suitable means known to one skilled in the art, such as for example, passing the composite structure 26 through a drying zone where the composite structure 26 may be heated, exposed to a vacuum suction, or a combination of heat and vacuum suction. Heat may be applied, for example, by running the foam through a forced air oven, IR oven, microwave oven, or radiowave oven. Still another way drying may be accomplished by capillary dewatering. Drying may be accomplished by any combination of the above. The extent to which the composite structure 26 may be dried depends on the application. In certain embodiments, greater than 50% of the aqueous phase may be removed. In certain other embodiments greater than 90%, and in still other embodiments up to 100% of the aqueous phase may be removed during the drying process. The composite structure 26 may be dried such that there remains less than 10% moisture content in the composite structure 26. Less than 10% moisture content in the composite structure 26 may be preferable to lessen the possibility of microbial or mold growth.

The absorbent foam particulates 16 may contract, expand, or remain the same size, after drying, depending upon the material used to form the particulates. Once the absorbent foam particulates 16 contract or expand upon drying, there may be a resulting void volume 59 within the enclosed valleys 54. This void volume 59 may allow for any fluid to be absorbed to collect within the void volume 59 until it is ready to be absorbed by the absorbent foam particulates 16. As shown in both FIGS. 7A-7B, these elements are common to both representations.

FIG. 7A describes a composite structure 26 where the absorbent foam particulates 16 contract after drying, resulting in a greater amount of void volume 59 within the enclosed valleys 54.

FIG. 7B describes a composite structure 26 where the absorbent foam particulates 16 have a lesser amount of void volume 59 within the enclosed valleys 54. The lesser amount of void volume 59 may be caused by using absorbent foam particulates 16 that remain the general same size after drying or by the expansion of absorbent foam particulates 16 after contracting fluids.

FIGS. 8-11 represent the methods 46 as discussed above.

Figure 8:
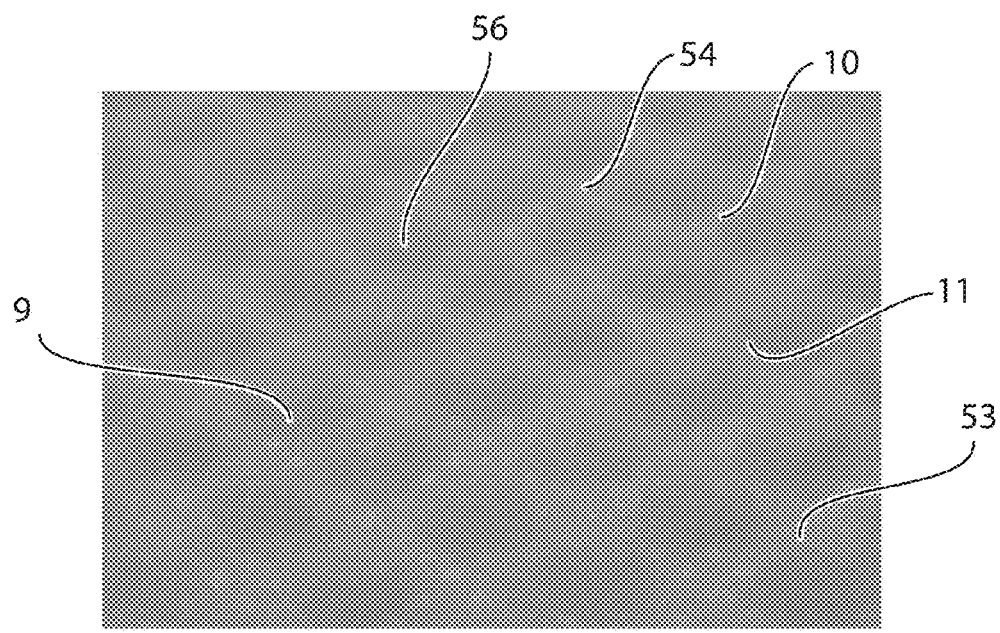
FIG. 8 is a top view image of a magnified view of a SELFed web.

FIG. 8 represents a top view image of a magnified view of a SELFed web. The SELFed web in FIG. 8 may serve as material for a carrier substrate 10. The SELFed web may have a pre-determined pattern 11. The pre-determined pattern 11 may have z-directional deflections 9. The SELFed web 10 may have peaks 56 and valleys 54. The SELFed web may have a carrier substrate first surface 53. The SELFed web may have a carrier substrate second surface (not shown).

Figure 9:
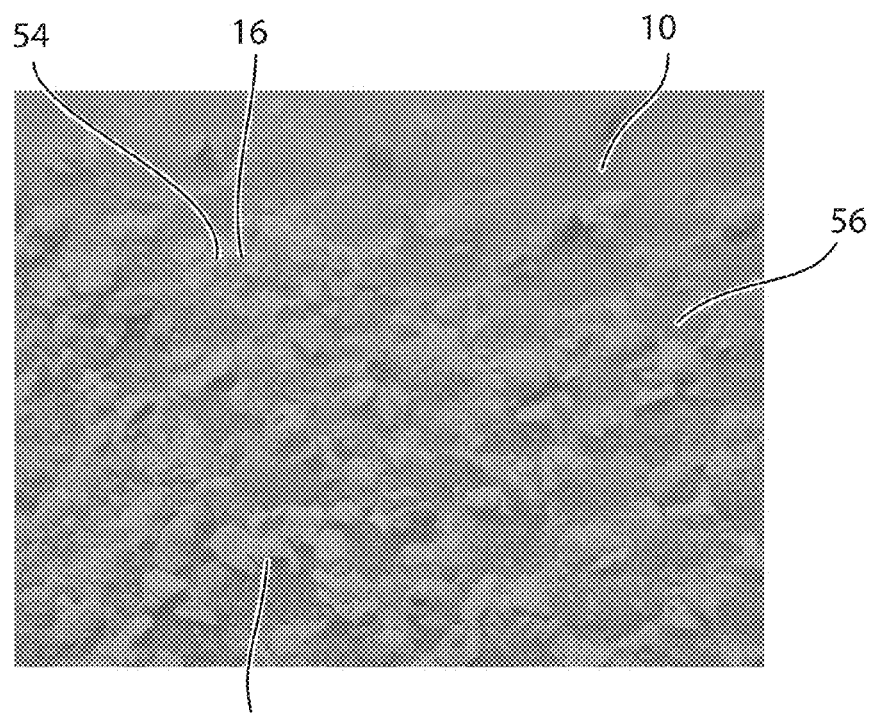
FIG. 9 is a top view image of a magnified view of a SELFed web after the particles have been settled.

FIG. 9 represents a top view image of a magnified view of a SELFed web after a particulate settling means (not shown) has affected the SELFed web. In FIG. 9, the SELFed web serves as the carrier substrate 10. A particulate settling means (not shown) may affect the carrier substrate 10, forming a settled carrier substrate 22. The particulate settling means (not shown) may be a vibration source (not shown). The vibration source (not shown) may be a vibrating table VJ-1212-10 supplied by the Cleveland Vibrator Company, Cleveland, Ohio. The vibration source (not shown) may relocate the absorbent foam particulates 16 from the peaks 56 to the valleys 54. The vibration source (not shown) may use a frequency of between about 25 Hz and 70 Hz and an amplitude of between about 104 micron and about 136 micron. The absorbent foam particulates 16 may be open-cell polymeric foam particulates. The absorbent foam particulates 16 may have a skeletal density between about 1.07 g/cm$^3$ and about 1.35 g/cm$^3$, a mean particulate size of between about 672 micron and about 740 micron, and a moisture content of between about 12.8% and 55%.

Figure 10:
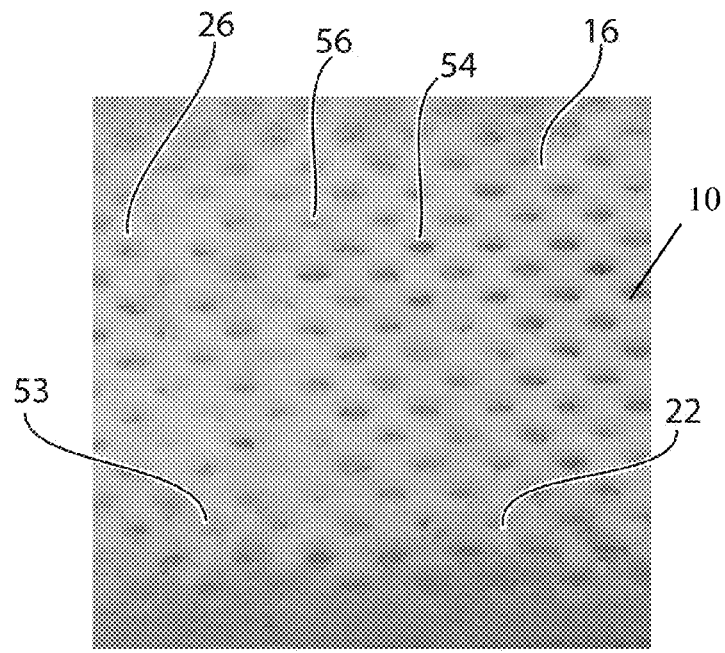
FIG. 10 is a top view image of a magnified view of a resulting composite structure.
Figure 11:
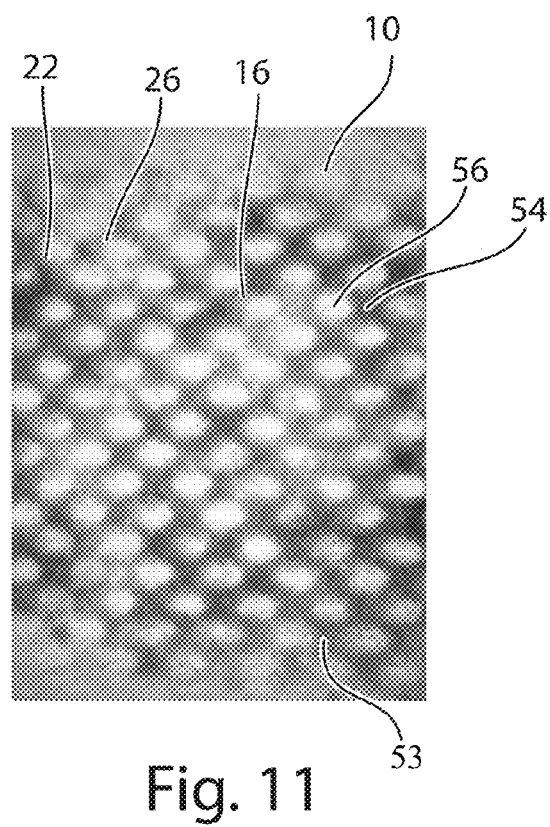
FIG. 11 is a top view image of a backlit magnified view of FIG. 10.

FIG. 10 represents a top view image of a magnified view of a resulting composite structure 26. FIG. 11 represents a top view image of a backlit magnified view of FIG. 10. The settled carrier substrate 22 may be associated with a cover substrate (not shown) by an adhesive source (not shown) to form a composite structure 26. The carrier substrate first surface 53 of the settled carrier substrate 22 may have peaks 56. The peaks 56 may be associated with the cover substrate (not shown) at bonding points (not shown). The carrier substrate first surface 53 of the settled carrier substrate 22 may have valleys 54. As shown, absorbent foam particulates 16 may be placed within the valleys 54.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosed method have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing composite structures with a plurality of absorbent foam particulates on a carrier substrate, the method comprising the steps of:
    a. providing the carrier substrate lying in an x-y plane, wherein the carrier substrate comprises a pre-determined pattern, wherein the pre-determined pattern comprises z-directional deflections;
    b. adding moisture to a plurality of absorbent foam particles;
    c. placing the plurality of absorbent foam particulates onto the carrier substrate, forming a loaded carrier substrate; and
    d. settling the loaded carrier substrate, forming a settled carrier substrate
    e. associating the settled carrier substrate layer with a cover layer, wherein the cover substrate is associated with the settled carrier substrate by a means of association.

2. The method according to claim 1, wherein the carrier substrate comprises non-woven material, film, paper web, structured webs, or combinations thereof.

3. The method according to claim 1, wherein the plurality of absorbent foam particulates comprise a plurality of High Internal Phase Emulsion (HIPE) foam particulates.

4. The method according to claim 1, wherein the plurality of absorbent foam particulates has a moisture content of less than 99.9%.

5. The method according to claim 1, wherein the plurality of absorbent foam particulates are settled using a particulate settling means, wherein the particulate settling means comprises a vibration source, doctor blade, doctor brush, vacuum, or combinations thereof.

6. The method according to claim 5, wherein the vibration source has a frequency of between about 5 Hz to about 200 Hz.

7. The method according to claim 1, wherein at least one of the settled carrier substrate or the cover layer is under tension, wherein the tension is between about 0.1 pounds per linear inch and about 1.0 pounds per linear inch.

8. The method according to claim 4, wherein the method further comprises drying the composite structure.

9. The method according to claim 1, wherein the composite structure is placed within an absorbent article.

10. The method according to claim 1, wherein at least one of the settled carrier substrate or the cover layer is liquid permeable.

11. The method of claim 1, wherein the means of association comprises adhesion, Velcro, or combinations thereof.

\* \* \* \* \*